United States Patent
Wilson

(10) Patent No.: US 9,980,856 B2
(45) Date of Patent: May 29, 2018

(54) STACKABLE SANITARY PADS

(76) Inventor: Brenda J. Wilson, Farmington Hills, MI (US)

( * ) Notice: Subject to any disclaimer, the term of this patent is extended or adjusted under 35 U.S.C. 154(b) by 0 days. days.

(21) Appl. No.: 13/485,865

(22) Filed: May 31, 2012

(65) Prior Publication Data

US 2012/0310202 A1     Dec. 6, 2012

Related U.S. Application Data

(60) Provisional application No. 61/491,552, filed on May 31, 2011.

(51) Int. Cl.
   *A61F 13/15*     (2006.01)
   *A61F 13/20*     (2006.01)
   *A61F 13/474*     (2006.01)
   *A61F 13/551*     (2006.01)

(52) U.S. Cl.
   CPC ........ A61F 13/474 (2013.01); A61F 13/5515 (2013.01)

(58) Field of Classification Search
   CPC .............................. A61F 13/474; A61F 13/505
   USPC .................. 604/382, 385.01, 385.03, 385.04
   See application file for complete search history.

(56) References Cited

U.S. PATENT DOCUMENTS

| | | | |
|---|---|---|---|
| 2,929,379 A | 7/1957 | Poulsen | |
| 3,367,334 A | 2/1968 | Testa | |
| 4,690,680 A * | 9/1987 | Higgins | 604/386 |
| 5,429,631 A | 7/1995 | Grenier | |
| 5,460,624 A | 10/1995 | Ahr et al. | |
| 5,507,735 A * | 4/1996 | Van Iten | A61F 13/474 604/385.05 |
| 5,599,339 A * | 2/1997 | Horney | 604/387 |
| 5,720,738 A * | 2/1998 | Clark | 604/385.01 |
| H1724 H * | 4/1998 | Ahr | 604/385.101 |
| 5,820,616 A * | 10/1998 | Horney | A61F 13/474 604/378 |
| 5,843,254 A * | 12/1998 | Clark | 156/66 |
| 5,849,003 A * | 12/1998 | Olsen et al. | 604/387 |
| H1788 H * | 2/1999 | Christon et al. | 604/385.101 |
| 5,910,137 A | 6/1999 | Clark et al. | |
| 6,280,427 B1 | 8/2001 | Maggiulli | |
| 6,395,956 B1 * | 5/2002 | Glasgow | A61F 13/4702 604/378 |
| 6,443,932 B1 | 9/2002 | Maggiulli | |
| 6,730,067 B1 * | 5/2004 | Nukina et al. | 604/385.01 |
| 6,840,926 B2 * | 1/2005 | Nukina et al. | 604/385.03 |
| 2009/0209927 A1* | 8/2009 | Ito et al. | 604/359 |

* cited by examiner

*Primary Examiner* — Michele M Kidwell
(74) *Attorney, Agent, or Firm* — The Weintraub Group, P.L.C.

(57) ABSTRACT

An absorbent multi-layer hygiene product comprising a plurality of stacked absorbent pads that are releasably attached to each other. Each absorbent pad includes a liquid-pervious topsheet, a liquid-impervious backsheet, and an absorbent core positioned between the topsheet and the backsheet. Each topsheet and backsheet extends beyond the absorbent core and forms an outer peripheral edge to sandwich the absorbent core. Each peripheral edge includes a pair of opposed longitudinal edges and a pair of opposed end edges. Each backsheet has a garment-facing surface and an adhesive disposed on the peripheral edge of the garment-facing surface to releasably secure the adjacent layers to each other.

3 Claims, 2 Drawing Sheets

STACKABLE SANITARY PADS

CROSS REFERENCE TO RELATED APPLICATION

This application claims the benefit of U.S. Provisional Application 61/491,552, which was filed on May 31, 2011, the disclosure of which is hereby incorporated by reference.

BACKGROUND OF THE INVENTION

1. Field of the Invention

The present invention relates to a multilayered absorbent hygiene product. More particularly, it relates to a stacked or layered product containing individual absorbent pads which are releasably attached one to another.

2. Description of the Prior Art

Absorbent products have long been used as feminine hygiene products. Discretion in the use of these products has been a goal of manufacturers and users alike. Absorbent pads and napkins used for feminine hygiene provide some specific capacity for absorbing body fluids. Once soiled, a product must be replaced by an unsoiled product. Unfortunately, a woman is not always at home or otherwise conveniently near a supply of these absorbent products, and it may be necessary for her to keep a minimal supply of products with her. Thus, feminine hygiene products have been manufactured to be carried conveniently in a woman's purse or pocketbook. These products have also been manufactured in convenient, individual packages to keep the product clean until use. However, more discrete ways to keep a ready supply of feminine hygiene products handy are constantly sought.

U.S. Pat. No. 2,929,379 to Poulsen suggested that a woman might carry a supply of three sanitary napkins in a sanitary napkin product having multiple layers. Aside from the multiple layers of absorbent pads which made up the sanitary napkin product, it incorporated cloth tabs which extended from the front and rear of the absorbent pad which were secured to a belt. This belt was separately worn about the user's waist. The use of the belt in conjunction with sanitary napkins allowed the napkins to be held closely to the user's body. The plurality of absorbent layers of the Poulsen product are stacked and attached in one general location proximate the front of the sanitary napkin product. The back of the upper individual layers was not anchored to the adjacent layer. It was constrained only by the nature of the belted product.

In more recent times, belted feminine hygiene products have generally been replaced by products which are releasably secured to a user's undergarments by means of a layer or strip of pressure sensitive adhesive disposed upon a garment-facing surface of the product. In addition, new and thinner products, including thin sanitary napkins and panty liners, have been developed. Panty liners may be used for applications other than those for which traditional sanitary napkins were designed. These feminine hygiene products are substantially thinner than conventional sanitary napkins and have a substantially concentrated absorbent volume. Thin feminine hygiene products therefore, have less of the absorbent fluff layer which helps to provide flexibility to the product.

Most feminine hygiene products have a body-facing absorbent side and a garment-facing barrier side. One or more lines of a pressure-sensitive adhesive are generally disposed on the garment-facing side to provide attachment means to removably affix the product to the garment. This pressure-sensitive adhesive is protected from contamination until use with a piece of release liner. When the product is to be used, the user must first remove the release liner and dispose of it. The disposal of a piece of release liner with each panty liner increases the waste generated by the use of these products. Thus, it is desirable to reduce the amount of release liner used in conjunction with panty liners in an era of increased environmental awareness.

Absorbent products have a finite absorbent capacity, and they must be periodically replaced. Manufacturers continue to search for products which are easily carried by a user, and which are convenient and discrete. One solution is discussed in U.S. Pat. No. 5,910,137 to Clark et al., which discloses a panty liner product having three single layers stacked and secured together. The bottom panty liner has a conventional adhesive disposed for positioning the product in the crotch area of a user's undergarment. Each remaining layer is releasably attached to the layer below it in the stack by adhesive or embossing (heat sealing) means. This illustrates that the adhesive is to be applied in two relatively small areas proximate the front and rear ends of the layer, or adjacent layers may be embossed at four discrete positions of the layers.

Additionally, Clark et al. also discloses a multilayered sanitary napkin product having smaller pads stacked on top of larger pads and secured with two discrete strips of adhesive tape. Again, these strips are at the ends of the pad layers.

After a substantial amount of research into the problems associated in developing panty liners having several removable absorbent layers, it has been discovered that panty liners having only one local attachment point between individual layers are susceptible to substantial movement of the unsecured portions of the panty liner layers. The forces acting on such pads tend to displace at least the topmost pad as the user moves. The displacement allows the pad to intrude into the area between the buttocks where it can be wedged, causing discomfort and painful chafing. This movement presents a major problem for users of thinner panty liners. Merely adding a second minor spot of adhesive cannot guarantee a firm attachment of the topmost panty liner through intermediate panty liner layers to the user's undergarment.

Using two small areas of adhesive spaced apart at the ends of a panty liner pad presents an additional problem. The adhesive may effectively attach adjacent pads at the adhesive application sites, but the adhesive cannot always prevent separation of the pads away from the application sites. Thus, when the application sites are located at the panty liner pad ends, the center section of adjacent pads can separate, causing problems similar to those identified above. Finally, while it is important that the absorbent layers of the panty liner product be secured together, the final product should be flexible enough to generally conform to the user to reduce chafing and other irritation.

Therefore, a new and useful panty liner product is needed having a plurality of absorbent pads which are releasably attached together in a secure manner. It is desirable that the product be flexible and comfortable to wear.

SUMMARY OF THE INVENTION

The present invention relates to an absorbent feminine hygiene product configured for releasable attachment to an undergarment. The product has several individual absorbent pad layers releasably joined together. Each of the absorbent pads has an absorbent layer and a liquid-impermeable barrier layer. An upper surface of each absorbent pad is defined by the top surface of the absorbent layer. A bottom, garment-facing surface of a first absorbent pad is configured for releasable attachment to a user's undergarment. A bottom surface of a second absorbent pad is releasably attached to the top absorbent surface of the first absorbent pad in a manner to prevent separation of significant portions of the absorbent pads during use.

In a preferred embodiment of the invention, there are provided at least three sanitary pads stacked atop each other, the bottom-most pad including a pair of wings or tabs extending laterally outwardly along the length of the pad for securement to a user's undergarment, each sanitary pad having an outer peripheral edge which includes an adhesive attached to the bottom thereof for releasably securing the pad to the adjacent pad therebelow, or to the undergarment in the case of the bottom-most pad.

Preferably, the absorbent pads are releasably attached using attachment means along the outer periphery of the pads. This application pattern keeps the individual pad layers of the product secured one to another and prevents gapping, curling, and other separation during use. The first absorbent pad can be releasably attached to a user's garment with a first separation force, and the second absorbent pad can be releasably attached to the first absorbent pad with a second separation force, less than the first separation force.

While individual pad layers are secured to adjacent layers, the individual pad layers can, nonetheless, slip along one another when subjected to shear forces because the adhesive is along the outer periphery of each pad. This allows the absorbent product of the present invention to remain as flexible as some single pad absorbent products of the same class which are commercially available.

Unless otherwise stated, when used in conjunction with adhesive coating and/or terms relating to surface areas, the term "coverage" and related forms of the word including the verb "to cover" as used in the specification and claims includes both a continuous layer of adhesive and a regular or random pattern of an adhesive coating having void areas. In particular, "coverage" includes the application of a pattern of discrete dots, fibrils, continuous or discontinuous lines, etc., over an area or substantially enclosing an area, even if the adhesive particles, fibers, etc., coat only a fraction of that area. Thus, the area "covered" by an adhesive is that area defined by the boundaries of the applied adhesive pattern.

For a more complete understanding of the present invention, reference is made to the following detailed description and accompanying drawings. In the drawings, like reference characters refer to like parts throughout the views in which:

DETAILED DESCRIPTION OF THE PREFERRED EMBODIMENT

Figure 1:
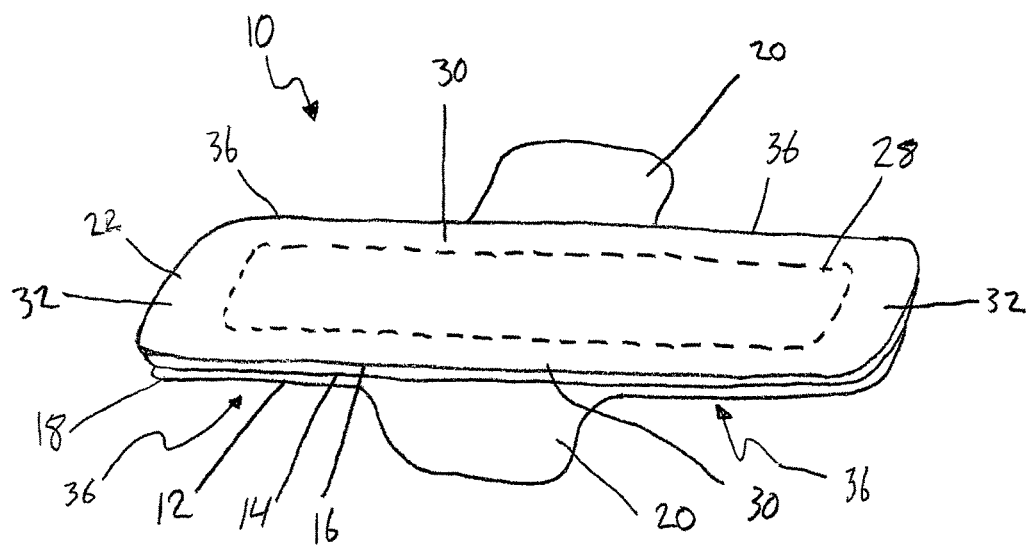
FIG. 1 is a perspective view of a first embodiment of the present invention hereof.

At the outset, it is noted that while the following discussion is made with specific reference to sanitary napkins or pads, the present invention can be used with panty liner products, thin incontinence pads, diapers, or any other similar type of absorbent product which is suitable for use herewith. The stackable nature of the product and the unique attachment means are not intended to be limited regarding the specific types of absorbent products discussed hereinbelow.

The absorbent product 10 of the present invention comprises a plurality of releasably attached absorbent pads 12, 14, 16 which are stacked together. The pads 12, 14, 16 may be attached by any means which provide sufficient attachment strength to maintain product integrity during use. Preferably, the stacked pads 12, 14, 16 are held together in a manner to prevent separation of significant portions of the absorbent pads during use. Thus, an attachment means 18 should be able to continue to hold adjacent pads together under both shear and peel forces likely to be encountered during product use.

The attachment means 18 may be adhesive, thermal or compressive such as heat sealing and embossing, or mechanical, such as fiber entanglement or hook-and-loop type fasteners.

Optionally the attachment means 18 can provide varied attachment strength between adjacent pads 14, 16, and between the bottom pad 12 and the user's garment to which it is attached. For instance, the first, garment-facing pad 12 may be releasably attached to the user's garment with a first attachment strength. The second absorbent 14 pad may be releasably attached to the first pad 12 with a second attachment strength which is preferably less than the first attachment strength. Additional pads may be releasably attached in a stacked manner to the top of the second absorbent pad 14 with successively decreasing attachment strengths. In this regard, the uppermost pad can be easily peeled from its adjacent pad while leaving the lower pads securely in place because less force is required to remove the uppermost pad than any of the lower pads.

The absorbent pads 12, 14, 16 which are stacked in the absorbent product may be of any geometry normally used in the feminine hygiene field, including strip-like, dog-bone, hourglass-shaped, or the like. The pads 12, 14, 16 may also have laterally extending tabs, or wings, 20 proximate a center portion of the pad for at least partially wrapping around a user's undergarment. It is understood that the tabs 20 have an adhesive on the lower side (not shown) to secure the tabs 20 to and around the undergarment. In the stacked multilayered absorbent product 10, each pad 12, 14, 16 may have at least substantially similar geometry, i.e., all strip-like or hourglass shaped. As used herein, the term "at least substantially similar geometry" includes, but does not necessarily mean, identical geometry. Where the pads 12, 14, 16 are of substantially similar geometry, they may optionally have slightly different proportions. Thus, successive absorbent pads may be proportionately longer or shorter in length. Alternatively, the pads may have different geometry. For example, only the first, garment-facing absorbent pad 12 might have tabs. In another embodiment, the ratio of length to width may be substantially altered, e.g., one layer long and narrow, and a second layer shorter and/or wider than the first.

The geometry of the individual absorbent pads 12, 14, 16 may therefore optionally allow for partial or complete overlap of one absorbent pad in relation to an adjacent pad. Preferably, at least a portion of a peripheral edge 22 of an upper absorbent pad overlaps at least a portion of an adjacent lower absorbent pad in the stacked product. This overlap can protect the lower pad from soiling or staining by bodily fluids during use and facilitates the removal of a soiled pad from the pad immediately below it. When the absorbent product 10 is constructed from identically-sized individual pads, the overlap of at least one edge of the uppermost pad may be achieved by staggering the pads (not shown). When the pads 12, 14, 16 are of different sizes, the pads 12, 14, 16 may be stacked in a manner to cover each pad with the absorbent pad immediately above it. Thus, the first, garment-facing pad 12 may be completely covered by a second absorbent pad 14, and a third absorbent pad 16 may completely cover the second absorbent pad 14. Additionally, each upper pad may extend beyond the peripheral edge 22 of the pad immediately below it in the stack.

The individual absorbent pads 12, 14, 16 of the multilayered product 10 are preferably sanitary napkins. This allows several absorbent pads 12, 14, 16 to form an absorbent product which will not be too thick for the average product user. As discussed above, the individual pads 12, 14, 16 may be panty liners, thin sanitary napkins, ultrathin sanitary napkins, incontinence pads, or even diapers. Optionally, the pads 12, 14, 16 can be flushable to further increase the invention's ease of use.

The absorbent product 10 of the present invention remains flexible. Thus, the multilayered absorbent pads 12, 14, 16 have a flexural resistance in the range of conventional sanitary napkins, and the multilayered panty liners have a flexural resistance in the range of conventional panty liners. Preferred multilayered panty liners have a flexural-resistance of less than about 0.25 lbs, and more preferred multilayered panty liners have a flexural resistance of less than about 0.2 lbs.

Figure 2:
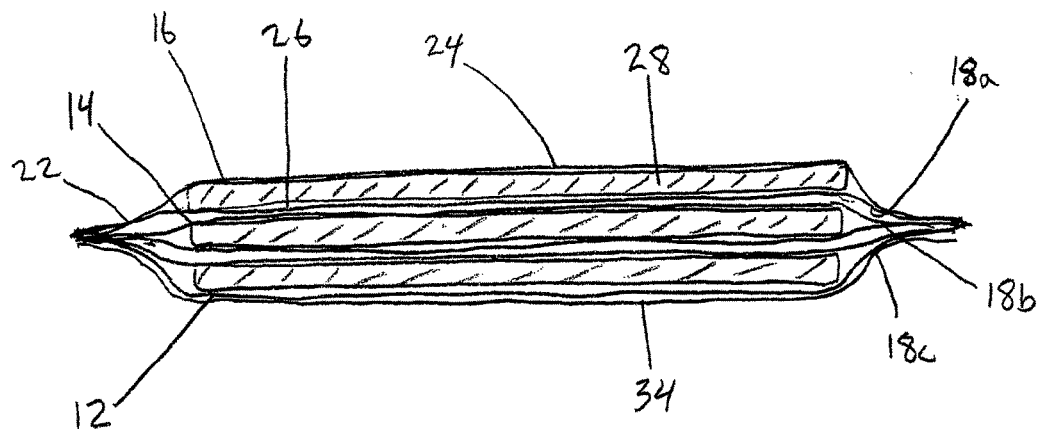
FIG. 2 is a cross-sectional view of a first embodiment showing the topsheet, absorbent core, and backsheet of each pad as assembled to form the absorbent product.

Each absorbent product 10 includes at least the top pad 16, the medial pad 14, and the bottom pad 12. FIG. 2 shows a cross section of the multilayered sanitary napkin, including the attachment means 18, for example adhesive 18a, 18b, which releasably attaches the top pad 16 to the center pad 14 and the center pad 14 to the bottom pad 12, respectively. In addition, the bottom pad 12 has an adhesive 18c for securement to the user's undergarment.

The present invention can use any suitable type of sanitary napkin, such as any sanitary napkin which is similar to the commercially available thin napkins sold under the trademarks KOTEX® Maxi Pads, KOTEX® Ultra Thin, STAYFREE®, CAREFREE®, ALWAYS®, etc. These products generally have a liquid permeable overwrap which encloses an absorbent structure and a liquid impervious barrier sheet (not shown). The overwrap is sealed together about the periphery or at the ends of the product. The materials of the exterior surfaces of thin sanitary napkins may be similar to those used in panty liners. The sanitary napkin may be about 6 to 13 inches (15 to 33 cm) long and about 2 to 5 inches (5 to 13 cm) wide.

When the absorbent pads 12, 14, 16 comprise a sanitary napkin, each sanitary napkin preferably comprises a liquid pervious topsheet 24, a liquid impervious impermeable backsheet 26 which is joined with the topsheet 24, and an absorbent core 28 positioned between the topsheet 24 and the backsheet 26.

The sanitary napkin has two surfaces, a body-contacting surface (or body-facing surface or "body surface") and a garment-facing surface (or garment surface). The body surface is intended to be worn adjacent to the body of the wearer while the garment surface is on the opposite side and is intended to be placed adjacent to the wearer's undergarments when the sanitary napkin is worn. It is to be understood that when the pads 12, 14, 16 are stacked atop each other, the garment-facing surface of the top pad 16 is positioned against the top surface of the medial pad 14, and the garment-facing surface of the medial pad 14 is positioned against the top surface of the bottom pad 12.

The sanitary napkin has a periphery 22 which is defined by the outer edges of the sanitary napkin in which the longitudinal edges are designated 36 and the end edges are designated 32.

Preferably the topsheet 24 and the first backsheet 26 of the sanitary napkin have a length and width dimensions generally larger than those of the absorbent core 28. The topsheet 24 and the backsheet 26 extend beyond the edges of the absorbent core 28 to thereby form portions of the periphery, or peripheral edge 22, thereby sandwiching the absorbent core 28 between the topsheet 24 and the backsheet 26. The edges 22 of the topsheet 24 and the backsheet 26 are secured to each other using any suitable means or well-known adhesive to form the peripheral edge 22.

The absorbent core 28 may comprise any absorbent means which are capable of absorbing or retaining liquids (e.g., menses and/or urine). The absorbent core 28 has a body surface, a garment surface, and longitudinal and side edges.

The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles, such as comminuted wood pulp which is generally referred to as "airfelt." Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied, for instance, the absorbent core may have varying caliper zones (e.g., profiled so as to be thicker in the center), hydrophilic gradients, superabsorbent gradients, or lower density and lower average basis weight acquisition zones; or may comprise one or more layers or structures. The total absorbent capacity of the absorbent core 28 should, however, be compatible with the design loading and the intended use of the sanitary napkin. Further, the size and absorbent capacity of the absorbent core 28 may be varied to accommodate different uses such as incontinence pads, pantiliners, regular sanitary napkins, overnight sanitary napkins, or adult diapers.

Exemplary absorbent structures for use as the absorbent core 28 of the present invention are described in U.S. Pat. No. 4,950,264 Osborn; U.S. Pat. No. 4,610,678 to Weisman et al.; U.S. Pat. No. 4,834,735 to Alemany et al.; and U.S. Pat. No. 5,972,487 to Duenk, et al. Each of these patents is incorporated herein by reference.

The topsheet 24 is compliant, soft feeling, and non-irritating to the wearer's skin. Further, the topsheet 24 is liquid pervious to permit liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet 24 because they are both pervious to body exudates and non-absorbent. They also have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 to Thompson; U.S. Pat. No. 4,324,246 Mullane, et al.; U.S. Pat. No. 4,342,314 to Radel et al.; U.S. Pat. No. 4,463,045 to Ahr et al.; and U.S. Pat. No. 5,006,394 to Baird. Each of these patents are incorporated herein by reference. The preferred topsheet 24 for the present invention is the formed film described in one or more of the above patents and marketed on sanitary napkins by The Procter & Gamble Company under the trademark DRI-WEAVE®.

The absorbent pads 12, 14, 16 generally and particularly described above are stacked and releasably attached to form the absorbent product 10 of the present invention. The pads 12, 14, 16 may be attached by any attachment means which provide sufficient attachment strength to maintain product integrity during use. The attachment means 18 may be adhesive 18a, 18b, thermal or compressive such as heat sealing and embossing, mechanical such as fiber entanglement or hook-and-loop type, and the like.

Figure 3A:
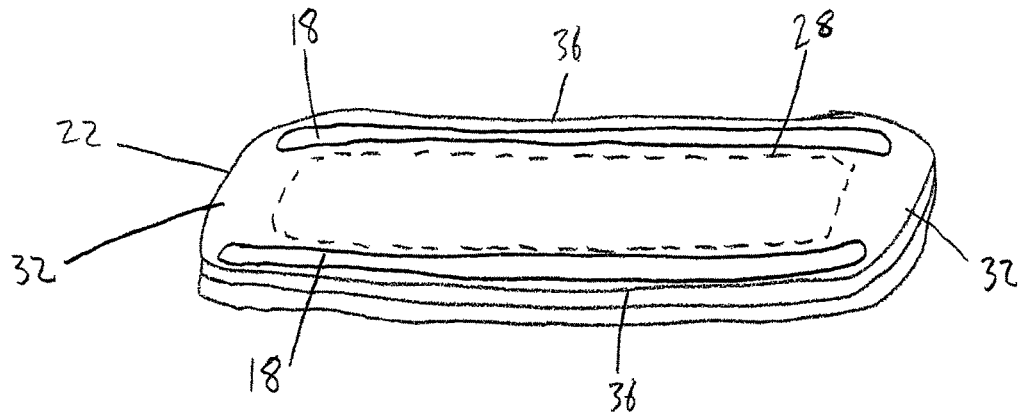
FIGS. 3A-3C show various exemplary positioning of the attachment means for securing the adjacent pads to each other.
Figure 3B:
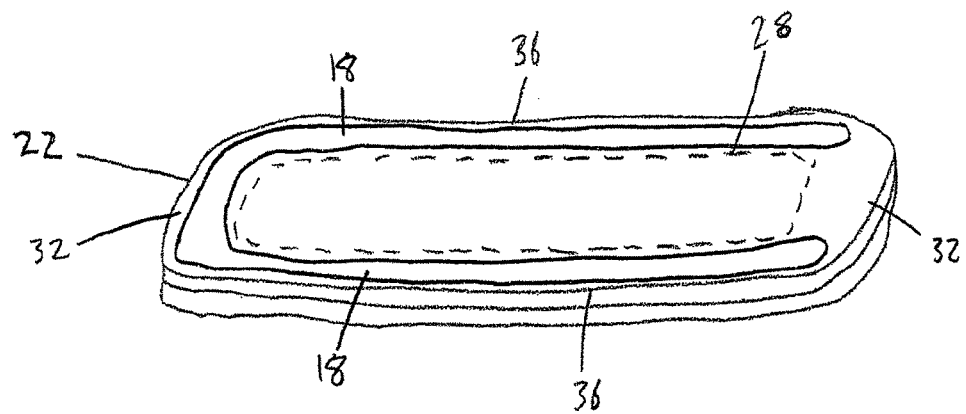
Figure 3C:
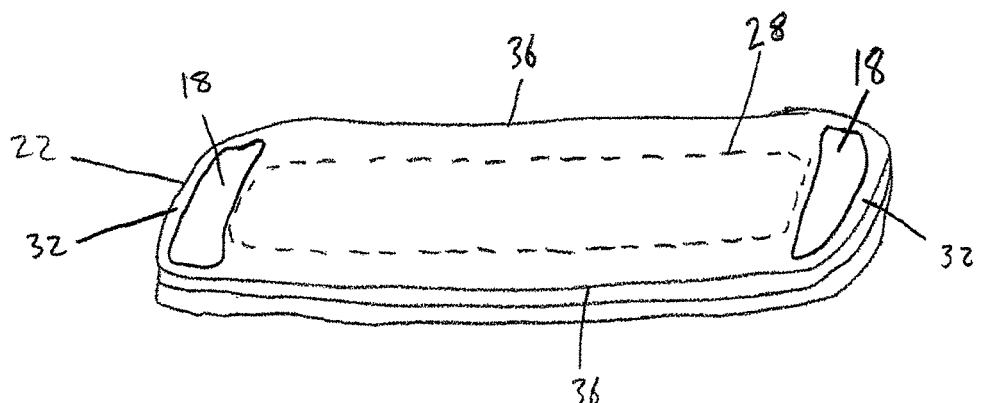

Optionally, the attachment means 18 may be a single attachment zone such as a solid area, a series of lines, a pattern of attachment points which cover an area, and the like. Preferably, the attachment means 18 comprises attachment zones which extend along the peripheral edge 22 of the pad. Even more preferably, the attachment means 18 comprises attachment zones which extend along the longitudinal edges 36 and one end edge 32 of the pad, thereby leaving the other end edge 32 of the pad without adhesive to allow the user to easily grab that edge for quick and easy removal of the uppermost pad. Shown in FIGS. 3A-3C are various exemplary positioning of the attachment means 18. It is to be understood that FIGS. 3A-3C are intended to be merely exemplary, and any other suitable positioning or orientation of the attachments means 18 can be used. Furthermore, unlike that in FIGS. 3A-3C, it is noted that the attachment means 18 are positioned on the bottom of each backsheet 26, not on the top of each topsheet 24. The attachment means 18 are shown in FIGS. 3A-3C on the top of each topsheet 24 simply to demonstrate the various configurations of the attachment means 18 that are possible.

In one preferred embodiment, the adhesive 18 may be applied to the backsheet 26 of an individual absorbent pad. Preferably, the adhesive 18 is disposed upon the outer peripheral edge 22 of the contact area of the backsheet 26. The adhesive 18 is also preferably applied at relatively low coating levels, i.e., low coating weights per unit area. The low coating weight over relatively large surface area provides a secure attachment between the adjacent absorbent pads 12, 14, 16 in the multilayered absorbent product 10.

It is noted that the adjacent absorbent pads 12, 14, 16 in the absorbent product 10 may optionally have a different adhesive strength to each other compared to the adhesive strength between the sanitary napkin and the garment to which it is attached. Preferably, the attachment strength between adjacent absorbent pads 12, 14, 16 can be less than the strength of the attachment means 18 between the sanitary napkin and the undergarment, although it does not need to be. In the case of adhesive attachment to the garment (positioning adhesive), this can be achieved by selective use of adhesives for both the layering adhesive and the positioning adhesive. For example, an adhesive which adheres more strongly to cotton than synthetic polymers would adhere more strongly to cotton undergarments. In a particularly preferred embodiment, the attachment strength between layers decreases with increasing vertical distance from the bottom pad 12. Thus, in a three-layered sanitary napkin, the positioning adhesive 18c or other attachment means between the product and garment can have the highest attachment strength, the attachment strength of the layering adhesive 18b between the bottom absorbent pad 12 and the center absorbent pad 14 can be less than the attachment strength between the bottom pad 12 and the undergarment, and the attachment strength of the layering adhesive 18a between the top pad 16 and the center pad 14 can be less than that between the center pad 14 and the bottom pad 12. In addition, the attachment strength between adjacent pads in the construction is preferably substantially less than the force necessary to delaminate the individual absorbent pads.

Optionally, the end edges 32 of the barrier film can lack adhesive, thereby providing finger tabs to enable a user to more easily separate adjacent absorbent pads 12, 14, 16. It may also be optional to provide wherein the longitudinal edges 36 of the barrier film can lack adhesive so that the uppermost pad can be removed by being grabbed along one of the longitudinal edges 36.

The layering adhesive 18 can comprise any suitable adhesive which is well-known to one having ordinary skill in the art. The layering adhesive 18 can be classified by method of setting: solvent-releasing, e.g., emulsion or organic solvent based; curing, e.g., radiation cure, electron beam, or catalytic cure; or hot melt. Preferred adhesives are pressure sensitive adhesives (PSA). PSAs can allow adjacent pads to be reattached if they are prematurely separated. However, PSAs have the potential of transferring to the cover material on an absorbent layer and forming a somewhat tacky surface on the cover material. Therefore, if a PSA is used as the layering adhesive, it is preferred that it be selected such that a minimal amount, if any, of the PSA transfers to the cover material from the barrier film. If a non-PSA is used, it is preferred that the adhesive remain flexible after setting so that the cover material remains supple and relatively soft to the touch.

Importantly, the layering adhesive 18 should not be aggravating or cause any adverse reaction (including any allergic reaction) when placed against skin for extended periods of time. This is particularly true when the layering adhesive 18 is a PSA because there is a potential for transferring the adhesive from an upper pad to the top of a lower pad. Many well-known PSAs which are suitable for use herewith are either hypoallergenic or known to generate few allergic reactions, such as acrylate or polyolefins.

A representative, non-limiting list of useful PSAs includes those based on natural rubber, styrene/butadiene latex, A-B-A block copolymer, butyl rubber and polyisobutylene, acrylics including vinyl acetate-acrylate copolymers, vinyl ether polymers, polyalkene polymers, polyurethane, ethylene-vinyl acetate copolymers and polypropylene including atactic polypropylene. A representative, non-limiting list of useful non-PSAs includes latexes based on the above-listed resins and hot melts based on these resins. Preferably, the adhesive is a PSA, and more preferably, the PSA is an A-B-A block copolymer, an acrylic resin, or an ethylene-vinyl acetate copolymer. Most preferably, the PSA is based on an A-B-A block copolymer. The adhesive 18 can be applied to the absorbent pad in any manner known to the ordinary practitioner. Such application methods include, without limitation, spraying, roll-coating, slot-coating, gravure rolling, etc.

The selection of the adhesive 18 for use as a layering adhesive is also dependent upon the composition of the backsheet 26 and the topsheet 24 of the individual absorbent pads 12, 14, 16 which make up the multilayered product 10. In particular, if a PSA is used, adhesive transfer can be noticeable. Also, if the topsheet 24 and backsheet 26 of adjacent absorbent pads 12, 14, 16 are formed from similar material, there may be a greater tendency for a PSA to transfer to the adjacent topsheet 24.

The choice of adhesive 18 used to practice the invention depends in part on the backsheet 26, and perhaps more particularly, the topsheet 24 used. The selection of adhesive 18 to use with a given topsheet 24 and backsheet 26 will be readily determined by one of ordinary skill in the art. Preferably, the adhesive 18 adheres strongly to the backsheet 26, less strongly to the topsheet 24 of an adjacent absorbent pad, and does not transfer from the backsheet 26 to the topsheet 24. As a guideline, it has been determined that A-B-A block copolymers work well with polyolefin backsheets 26 and nonwoven topsheets 24. These block copolymers also work with apertured film cover materials. Acrylics, EVA and other similar adhesives also work with these materials.

In use, the user removes a release liner 34 which protects the positioning adhesive 18c from the multilayered sanitary napkin, and secures the product 10 in the crotch area of the undergarment. After some period of time when the top absorbent pad 16 has become soiled, the user can simply remove the soiled pad to expose the next absorbent pad 14. This procedure can be continued until all absorbent pads have been soiled and a new multilayered product 10 is needed.

It is to be understood by one having ordinary skill in the art that the present invention can be used with a diaper in a manner in which the stackable pads (e.g., incontinence or diaper pads) are placed within the seat or crotch of the diaper itself to prolong the usable life of the diaper.

As is apparent from the preceding, the present invention provides a stacked or layered product containing individual absorbent pads which are releasably attached one to another and which provide a quick, clean, and efficient way of replacing an absorbent pad.

What is claimed is:

1. An absorbent multi-layer feminine hygiene product comprising:
    (a) at least three absorbent pads that are releasably attached to each other, the plurality of absorbent pads being arranged in a stack, each one of the plurality of absorbent pads including:
    (i) a liquid-pervious topsheet, a liquid-impervious backsheet, and an absorbent core positioned between the topsheet and the backsheet;
    (ii) each topsheet and backsheet having an outer peripheral edge extending beyond the absorbent core and forming an outer peripheral edge to sandwich the absorbent core between the topsheet and the backsheet, each peripheral edge including a pair of opposed longitudinal edges and a pair of opposed end edges; and
    (iii) each backsheet having a garment-facing surface and an adhesive disposed on at least a portion of the peripheral edge of the garment-facing surface;
    wherein the adhesives are disposed on each one of the pair of opposed end edges and the opposed longitudinal edges remain free of adhesive;
    and the adhesives are successively decreasing in attachment strength from the lowermost pad proximate an undergarment to the uppermost pad proximate a person's body to facilitate the individual removal of the uppermost pad from an adjacent, lower pad.

2. The absorbent multi-layer feminine hygiene product of claim 1 further comprising:
    a pair of tabs extending laterally from opposing longitudinal edges of a respective pad for at least partially wrapping around the undergarment, the pair of tabs having an adhesive disposed on a bottom surface thereof.

3. The absorbent multi-layer feminine hygiene product of claim 1 wherein the outer peripheral edge of the topsheet and the outer peripheral edge of the bottom sheet are sealingly engaged.

* * * * *